United States Patent
Chiu et al.

(10) Patent No.: US 7,256,542 B2
(45) Date of Patent: Aug. 14, 2007

(54) METHOD AND DEVICE FOR DETECTING MOISTURE IN ELECTROLUMINESCENCE DISPLAY DEVICES

(75) Inventors: Chun-Yi Chiu, Hsinchu (TW); Chih-Hung Su, Hsinchu (TW)

(73) Assignee: AU Optronics Corporation, Hsinchu (TW)

( * ) Notice: Subject to any disclaimer, the term of this patent is extended or adjusted under 35 U.S.C. 154(b) by 14 days.

(21) Appl. No.: 10/783,826

(22) Filed: Feb. 20, 2004

(65) Prior Publication Data

US 2005/0184661 A1    Aug. 25, 2005

(51) Int. Cl.
*H01L 51/00* (2006.01)
(52) U.S. Cl. .................. 313/512; 313/504; 313/506
(58) Field of Classification Search ........ 313/498–512; 428/690, 917; 257/59, 347
See application file for complete search history.

(56) References Cited

U.S. PATENT DOCUMENTS 4,344,062 A * 8/1982 Sudoh et al. .................. 338/35
6,635,988 B1 * 10/2003 Izumizawa et al. ......... 313/504

FOREIGN PATENT DOCUMENTS

| JP | 02-179449 | 7/1990 |
| JP | 05-240823 | 9/1993 |
| JP | 03-157970 | 5/2003 |

* cited by examiner

*Primary Examiner*—Karabi Guharay
*Assistant Examiner*—Anthony Canning
(74) *Attorney, Agent, or Firm*—Duane Morris LLP

(57) ABSTRACT

Methods and devices are disclosed for detecting undesired moisture for a luminescence display device. A moisture detector is encapsulated between two shields with one or more display elements, and has a layer of metal placed in a predetermined location close to the display elements that does not affect an operation thereof, wherein the undesired moisture is detected by monitoring one or more moisture-affected material characteristics thereof.

9 Claims, 3 Drawing Sheets

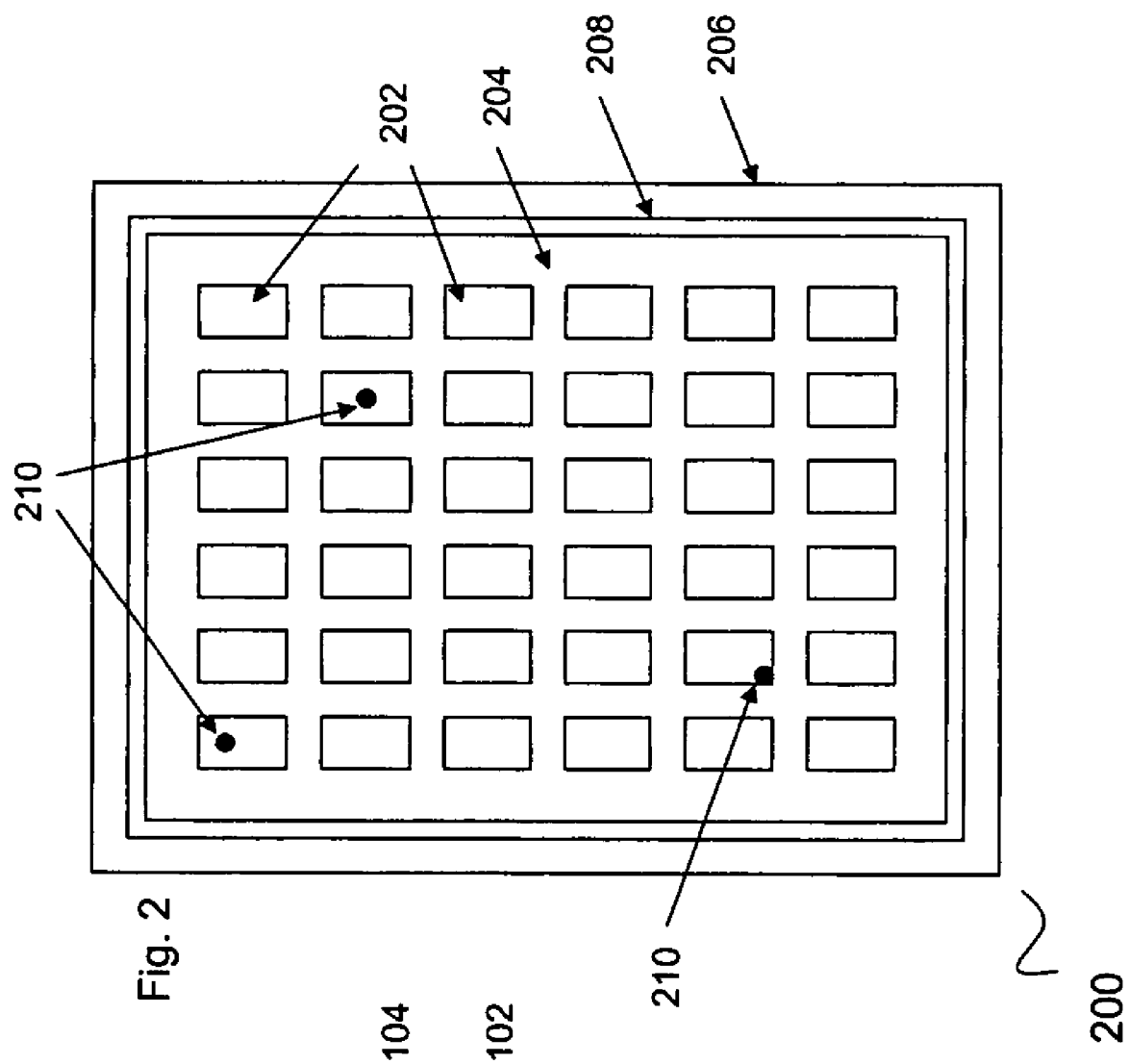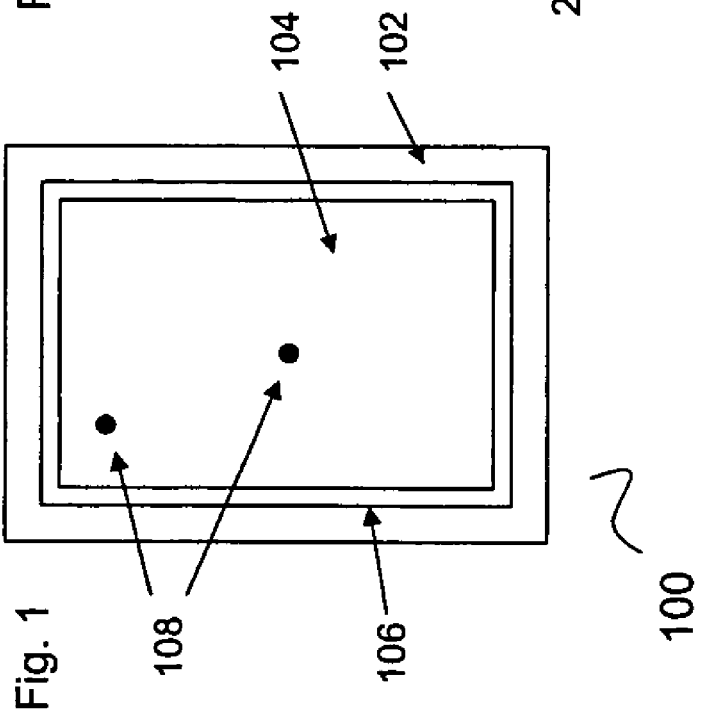

METHOD AND DEVICE FOR DETECTING MOISTURE IN ELECTROLUMINESCENCE DISPLAY DEVICES

BACKGROUND

The present disclosure relates generally to organic electroluminescence (EL) display devices, and more particularly to the detection of moisture within the sealed pixel elements and sealed display panels of the EL electro-optical display devices and the like.

Electroluminescence (EL) display devices comprise of a plurality of light emitting elements (pixels) which utilize electric field light emission of solid fluorescent substance or phenomenon called electroluminescence. The luminous material layers of an EL device is commonly applied in the backlight of liquid crystal, flat panel, electro-optical displays which may be either transmissive, reflective and/or transflective. Advanced technology EL pixels utilize organic light emission diodes (OLEDs) featuring the use of organic polymer material compound layers as the luminous material layers of the devices. The use of the organic polymer layers, as opposed to the previous usage of inorganic material layers, offer improvements to the display devices' display performance, operational efficiencies, package sizing/portability, as well as reduction in power and voltage requirements.

Organic EL elements such as OLEDs are much more sensitive to degradation issues related to ambient environment conditions such as water moisture and free oxygen than inorganic EL elements. Specifically, water moisture and oxygen may cause undesired crystallization and formation of organic solids, undesired electrochemical reactions at the electrode-organic layer interfaces, corrosion of metals and the undesired migration of ionic species. It has been noted in research, that degradation due to water moisture is at least a thousand times more destructive than from free oxygen. These degradation mechanisms often manifest as the growth of dark spot defects upon the emissive display elements. Such defects may lead to performance loss, operational instability, poor color/emission accuracies, as well as shortened operational life. The dark spot defects are typically not immediately formed upon the display elements as their growth in quantity, size and location are based upon time exposure in the offending environment.

To minimize such degradation mechanisms, the organic EL elements are typically encapsulated in an attempt to prevent moisture migration to the active EL display elements. Typical encapsulation methods utilize a transparent, translucent shield covering the entire display element with an adhesive sealant used to seal the shield to the device substrate layer. For LCD as well as LED display panel devices, depending on the technology, the shield may encapsulate a plurality of display elements as opposed to, or in addition to the encapsulation of single or smaller group of display elements. It is noted that conventional sealing, encapsulation methods often trap some lower level of residual water moisture within the display device as efforts for total water moisture removal during the sealing, encapsulation processes are very difficult to accomplish.

Dark spot defects may still grow within encapsulated display elements due to various reasons. Encapsulation seals may be initially poor or themselves degrade in time, enough to lose their seal or encapsulation integrity. Poor initial seal and loss of seal integrity will allow water moisture to migrate to the organic EL display elements. The trapped, residual water moisture held within the encapsulated organic EL elements may also cause dark spot growth.

EL display device fabrication facilities typically implement environmental stress testing upon completed, fabricated display devices in attempt to accelerate the dark spots growth. Such accelerated testing methods using stress environments such as high temperatures (60-85 degrees Celsius) and high relative humidity (85-90% RH) allows the production facilities to visually inspect and judge their completed display device products for defectively encapsulated devices as well as providing relative judgment and extrapolation of seal integrity and expected lifetime. Limitation and inaccuracies to such described stress testing methods are very dependant upon and due to the manual, visual inspection procedures used to attempt the quantitative and qualitative analysis of the dark spot defects.

FIG. 1 is a top view of a typical organic EL device 100 to illustrate the application of the shield and adhesive sealant to encapsulate the display device. The device substrate 102 is shown covered with the encapsulation shield 104. The shield 104 may be a color filter or clear/transparent substrate, and covers the entire organic EL device with continuous lines of adhesive sealant 106 located on the device substrate 102 along the same directions as the length and width perimeters of the EL display device 100. The shield 104 is attached directly to the device substrate 102 utilizing the adhesive sealant 106 to encapsulate the EL display device 100. In summary, the encapsulation seal is accomplished primarily using a sealant between the bottom surface of the shield 104 and top surface of the device substrate 102. FIG. 1 also illustrates examples of dark spot defects 108 that have grown onto the display element of the EL device 100. There are two dark spots 108 shown to illustrate the randomness of quantity, size and location within the sealed display device.

FIG. 2 illustrates the top view of an organic EL display panel 200 that contains multiple EL display devices or display elements. Such a display panel contains multiple OLED elements 202 encapsulated between the shield 204 and device substrate 206. The shield 204 is sealed to the device substrate 206 with continuous lines of adhesive sealant 208 located on the device substrate 206. Dark spots 210 are shown located within the encapsulated display panel 200.

What is desirable is an improved method and/or test device for the detection of water moisture within encapsulated organic EL display devices and display panels.

SUMMARY

In view of the foregoing, this disclosure provides improved method and/or test device that will provide more sensitive and accurate data for the quantitative and qualitative analysis and judgment of the detrimental effects of water moisture upon and within the encapsulated display devices.

In one example, a device is disclosed for detecting undesired moisture for a luminescence display device. The device is encapsulated between two shields with one or more display elements, and has a layer of metal placed in a predetermined location close to the display elements that does not affect an operation thereof, wherein the undesired moisture is detected by monitoring one or more moisture-affected material characteristics thereof.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 illustrates a top view of a typical encapsulated organic EL display device with dark spots growth upon an emissive display element.

FIG. 2 illustrates a top view of a typical encapsulated organic EL display panel, comprised of multiple EL display elements with dark spots growth upon the emissive display elements.

DESCRIPTION

The present disclosure describes an improved method for the effective detection and monitoring of water moisture within encapsulated organic EL display devices and panels. The disclosed methods provide a water moisture detection device that could be incorporated within the encapsulated display devices and panels for sensitive and accurate quantification and qualification of the effects of water moisture, which affects one or more material characteristics thereof. Such an improved testing method and detector would be easily designed and implemented into existing display device designs, as well as into existing fabrication operations with minimal impact to additional costs and required processes. This disclosed method and device will lead to higher reliability and longer operational life of the devices.

Figure 3:
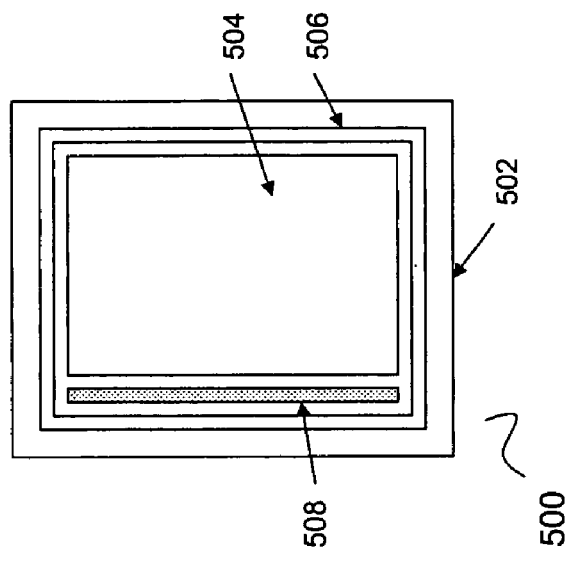
FIG. 3 illustrates a cross-sectional view of the water moisture detection device in accordance with an example of the present disclosure.

FIG. 3 illustrates a cross-sectional view of the water moisture detection device in accordance with an example of the present disclosure. The water moisture detector 300 is shown located on top of the device substrate 302. The detector 300 comprise of three basic material layers. A bottom electrode layer 306 is deposited on top of the device substrate 302 during the final fabrication processing operations of the organic EL display elements. The bottom electrode layer 306 may be comprised of the same metal compounds, aluminum-based or indium tin oxide (ITO) used respectively as the cathode and anode materials of the organic EL emissive display elements. The middle layer 304 of the water moisture detector is then deposited on top of the bottom electrode layer 306. This middle material layer 304 is comprised of metal compounds from either the group IA (Alkali) earth metals (which may include Li, Na, and K, etc.) or the group IIA (Alkaline) earth metals (which may include Be, Mg, and Ca, etc.) of the periodic table of elements.

Other than the use of metal compounds from either of the group IA or IIB earth metals, any other active metal that is likely to react with water can be used for the disclosed detector device. Thin layers (e.g., less than 200 angstroms) of the disclosed middle material layer 304 exhibit resistivity and transmissivity properties that are desirable for use in the detection of water moisture within the encapsulated organic EL display devices. Specifically, the thin layers of IA and IIA metal compounds are very responsive to water moisture exposure such that electrical resistivity and light transmissivity changes with very predictable and repeatable characteristic responses. The detector device can be manufactured on any spare regions of the display panel, and does not have to be limited by any particular location.

Figure 4:
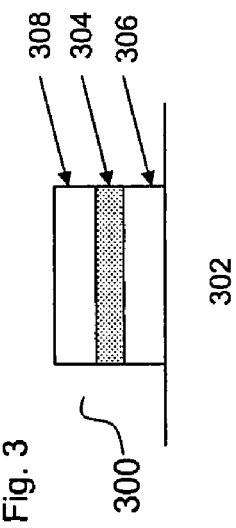
FIG. 4 is a graph to illustrate the relationship of resistivity as a function of time for the water moisture detection device in accordance with the present disclosure.

FIG. 4 is a data graph that illustrates the relationship of resistivity as a function of time for a water moisture detector constructed with a calcium compound middle layer 304 of predetermined dimensions (length, width and height). It is noted that the measured electrical resistivity of water moisture detector rises in time (hours) during continued exposure to a controlled environment of 60 degrees Celsius temperature and relative humidity of 90% RH. The continued exposure to the controlled water moisture environment causes the material properties of the middle layer 304 and it's interfaces with the adjacent electrode layers 306 and 308 to effectively change and raise the measured resistivity.

Referring back to FIG. 3, the last, top layer of the water moisture detector is the deposited top electrode layer 308. Similarly, as with the bottom electrode layer 306, this top electrode layer 308 may also be comprised of the same metal compounds, aluminum-based or indium tin oxide (ITO) used respectively as the cathode and anode materials of the organic EL emissive display elements. After the addition of the top electrode layer 308, the 3-layered stack of materials is patterned and etched to define the three dimensional (length, width and height) structure of the moisture detector. It is important to note that the characteristic resistivity-time relationship of the moisture detector will be primarily dependent upon, the three dimensional structure of the middle layer 304, the composition of the middle layer 304, the composition of the metal electrode layers 306, 308, and the water moisture environment conditions. When the resistance of this moisture detector has risen above certain threshold, it indicates that a predetermined level of moisture has "invaded" the display device.

Electrical resistance measurements of the moisture detector may be made and to quantify and qualify the water moisture content within the organic EL display device, as well as correlation to any performance degradation of the display device due to the effects of water moisture. The measured electrical resistance data may be compared to reference and characterization curves such as the example shown as FIG. 4 of the disclosure. The electrical test measurement may be optionally performed at anytime before, during, and after the display device sealing, encapsulation processes as long as the electrical connections to the top and bottom electrodes of the moisture detector are available for use. This flexibility in measurement opportunities allows for much additional data collection to be available for the characterization of the sealing, encapsulation processes of EL display devices.

Another moisture detection mechanism can be implemented using the light transmissivity property affected by the water moisture. A variation of the detector 300 may also be used for the sensitive and accurate quantification and qualification of the effects of water moisture upon organic EL display devices. Without using the electrode layers (i.e., the top and bottom layers) of the detector, a thin layer (<200 A) of IA and IIA metal materials can be used alone for moisture detection as it exhibits opaque variability at certain light wavelength ranges that is very responsive to water moisture exposure. Exposure of the material to water moisture causes changes to the material to become more transparent at certain light wavelength ranges such as ultraviolet (UV) or infrared (IR). Such transmissivity property changes of the material may be very predictable and repeatable characteristic responses that could be used to both quantify and qualify the effects of water moisture upon organic EL display devices. It is noted that the measurements of light transmissivity for the disclosed moisture detector would be performed through the display device's top and bottom packaging shields or substrates.

Figure 5:
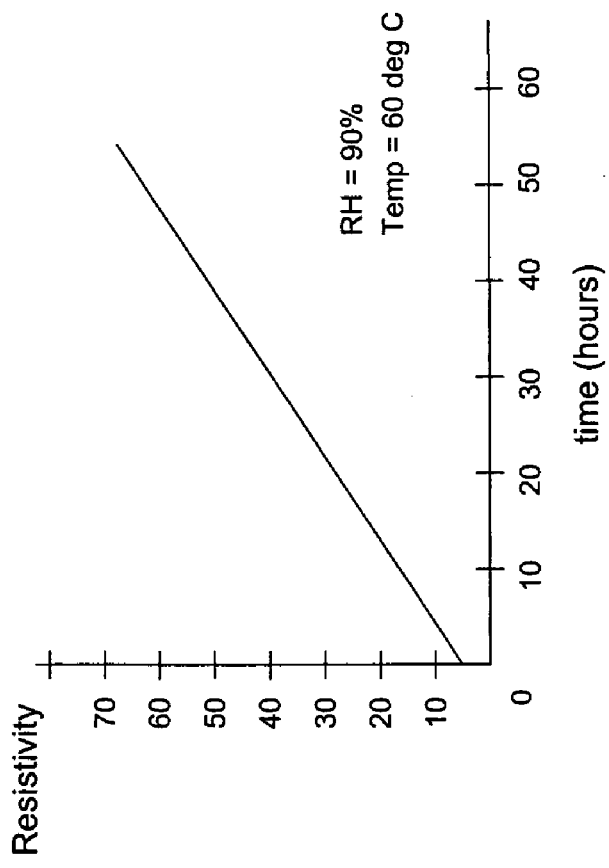
FIG. 5 illustrates a top view of an encapsulated organic EL display device incorporated with water moisture detection module in accordance with one example of the present disclosure.

FIG. 5 illustrates a top view of an encapsulated organic EL display device 500 incorporated with water moisture detection mechanism in accordance with the present disclosure. The device substrate 502 is shown covered with an encapsulation shield 504. The shield 504 covers the entire organic EL device 500 with continuous lines of adhesive sealant 506 located on the device substrate 502. In summary, the encapsulation seal is accomplished primarily using a sealant 506 between the bottom shield 504 and top shield 502. An example of the disclosed water moisture detector 508 is shown located adjacent to the active emissive display element within the encapsulated organic EL display device 500. The water moisture detector 508 in this example is only a strip of thin metal layer.

With the thin metal layer moisture detector installed in the EL display device, light transmissivity measurements may be performed upon the moisture detector 508 to help quantify and qualify the water moisture content within the organic EL display device 500. As the metal is oxidized by the water, the area in which the thin metal layer is placed become more transparent. As it can be appreciated, any metal can be used for the metal layer as long as it will react with water to turn itself into a material that would allow more light to transmit therethrough. For example, metals from family IA and IIA can be good candidates for this purpose. Similar to the electrical resistance measurements, the measured light transmissivity data may be compared to previously established reference and characterization curves. Transmissivity measurements may also be optionally performed at anytime before, during, and after the display device encapsulation processes as long as there is open path for the transmission of light through the moisture detector 508. The flexibility in measurement opportunities also allows for much additional data collection to be available for the characterization of the encapsulation processes of EL display devices.

Figure 6A:
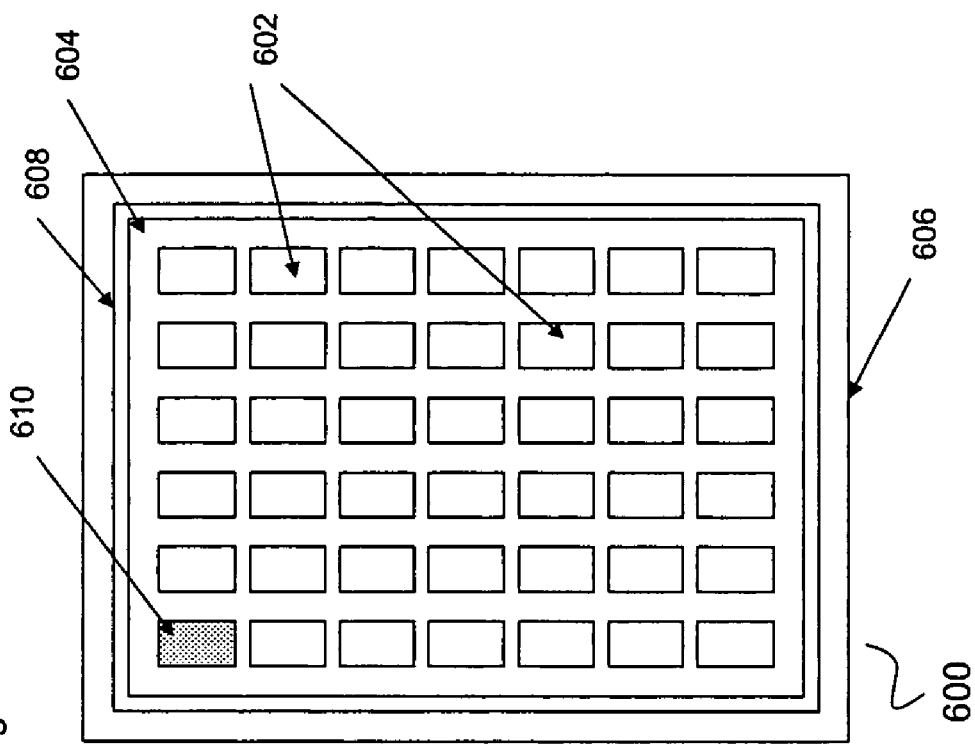
FIGS. 6A and 6B illustrate top views of two examples of encapsulated organic EL display panels incorporated with water moisture detection in accordance with the present disclosure.
Figure 6B:
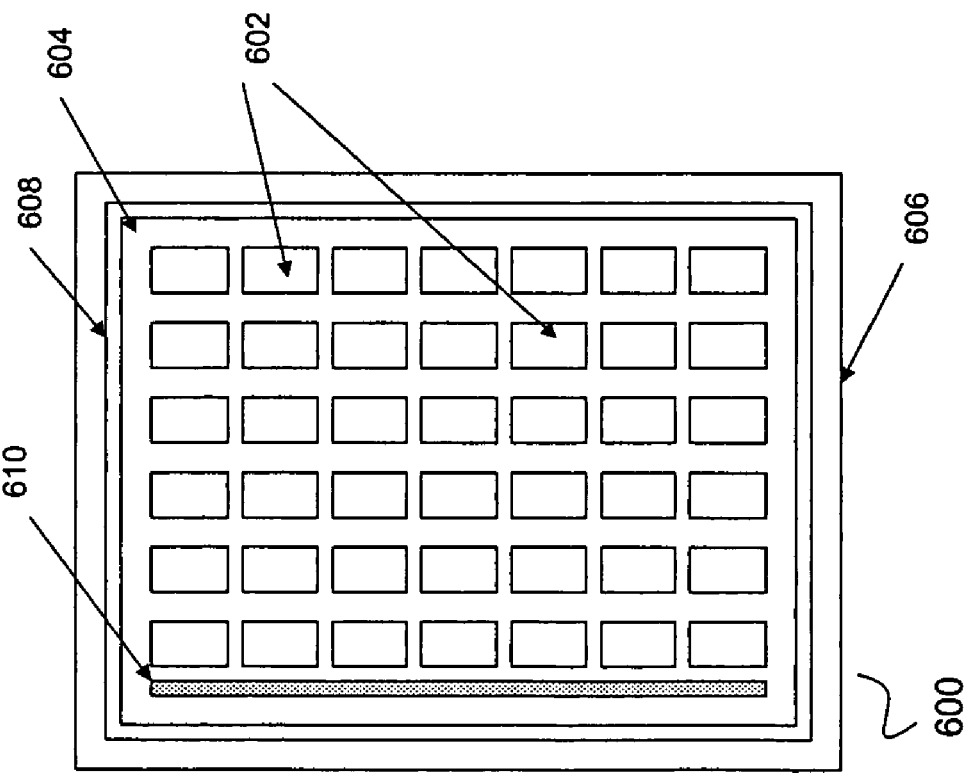

FIGS. 6A and 6B illustrate top views of two examples of encapsulated organic EL display panels, comprised of multiple EL display devices or display elements, with the incorporation of water moisture detectors in accordance with the examples of the present disclosure. Both display panels 600 contain multiple OLED elements or pixels 602 encapsulated within a first shield 604, which may be a glass shield, and a second shield 606, which may the back plane or receptacle of the display panel. The shield 604 may be sealed to the back plane 606 with continuous lines of adhesive sealant 608 located around the EL display panel 600.

In the example shown by FIG. 6A, the water moisture detector 610 is illustrated as a long structure running along the length of the display panel 600 corresponding to the length of the long column of multiple OLED display pixels 602. The location of this detector can be anywhere else as long as it does not affect the function of the display elements. In addition, it does not have to be of the same length of the column. Several shorter length detectors can function as the single long one.

FIG. 6B illustrates a similar display panel 600 with an example of another moisture detector 610 of different size and location within the encapsulated display device. The moisture detector 610 of FIG. 6B shows a detector placed in a display element region with x-y area dimensions approximately the same as the adjacent OLED display elements 602. The moisture detector 610 is located within and conforming to the array alignment of adjacent OLED display pixels 602. The detector 610 sizing and location shown in FIG. 6B may be preferred in some display panel designs to help maintain a small package and size for the completed organic EL display panel. The cost for placing such a "test chip" in the display panel is the waste of a small area in which a display element can be installed. However, in view of the number of display elements in the display panel, this is a very affordable solution in view of the benefits achieved. In addition, the location of this test chip can be anywhere as long as it does not affect the normal operation of the display panel. More than one of this type of moisture detectors can be placed in different parts of the display panel for accurately detecting the moisture encroachment.

The testing method utilizing the moisture detection devices as described above in accordance with the present disclosure will result with improved sensitivity and accuracy for the quantitative and qualitative analysis of the detrimental effects of water moisture upon and within encapsulated organic EL display devices and display panels. Comparing to the manual and visual inspections for dark spot defects on completed display devices, this disclosure provides means for systematically and even automatically detecting undesired moisture. The disclosed water moisture detection device incorporated within encapsulated display devices and panels allows for either the electrical (resistivity) and transmissivity (light) properties of the detector material to be used for the quality control of the organic EL display device fabrication processes, as well as the quality and performance of the final display device products. For example, water moisture can be detected "in-line" immediately after the packaging or device dicing process. The resistance or light transparency measurements allow for more accurate characterization of the defected devices so that the moisture detection can be automatically performed for a large number of devices.

Such improved testing methods and moisture detectors would be easily designed and implemented into existing display devices and panels, as well as into existing fabrication process operations with minimal impact to additional costs and required processes. This disclosed sensitive and accurate testing method and device will lead to higher reliability and longer operational life of the devices.

The above disclosure provides many different embodiments or examples for implementing different features of the disclosure. Specific examples of components and processes are described to help clarify the disclosure. These are, of course, merely examples and are not intended to limit the disclosure from that described in the claims. For example, the illustration above uses OLED devices as examples, but it should be appreciated that any display device that has moisture concern can implement similar moisture detection mechanisms by monitoring the moisture-affected material characteristics.

Although the invention is illustrated and described herein as embodied in a design and method for, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the disclosure, as set forth in the following claims.

What is claimed is:

1. An organic luminescence display device comprising:
   one or more display elements;
   at least one moisture detector placed in a predetermined location close to the display elements, the moisture detector including a material layer comprising metal formed between a first electrode and a second electrode; and
   a first and second shields for encapsulating the display elements and the moisture detector therebetween,
   wherein the material layer between the first and second electrodes of the moisture detector has a resistance that varies with a moisture level of an environment in which the display device is located.

2. The display device of claim 1 wherein the moisture detector is placed in the predetermined location of the device so that it does not affect an operation of the display elements.

3. The display device of claim 1 wherein a light transmissivity of the moisture detector varies with the moisture level of the environment in which the display elements are located.

4. The display device of claim 1 wherein the material layer comprises a metal compound.

5. The display device of claim 1, wherein each of the one or more display elements includes a cathode and an anode made of the same material as the first and second electrodes.

6. The display device of claim 1, wherein the material layer of the moisture detector contains a IA or IIA group earth metal.

7. The display device of claim 1, wherein the material layer has a thickness of 200 angstroms or more.

8. The display device of claim 1, wherein the display elements form an array, the moisture detector is located proximate to a column of display elements located at an edge of the array, and the moisture detector extends from a first position located proximate to a top edge of a top display element of the column of display elements to a second position located proximate to a bottom edge of a bottom display element of the column of display elements.

9. The display device of claim 1, wherein the display elements are disposed to form an array pattern comprising a plurality of element regions, and the moisture detector is disposed at an element region located at a corner of the array pattern.

* * * * *